(12) United States Patent
Naftali et al.

(10) Patent No.: US 7,184,612 B2
(45) Date of Patent: Feb. 27, 2007

(54) HARDWARE CONFIGURATION FOR PARALLEL DATA PROCESSING WITHOUT CROSS COMMUNICATION

(75) Inventors: Ron Naftali, Shoham (IL); Vitaly Rubinovich, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 486 days.

(21) Appl. No.: 10/698,533

(22) Filed: Nov. 3, 2003

(65) Prior Publication Data
US 2004/0089824 A1   May 13, 2004

Related U.S. Application Data

(62) Division of application No. 09/726,597, filed on Dec. 1, 2000, now Pat. No. 6,898,304.

(51) Int. Cl.
*G06K 9/54* (2006.01)
(52) U.S. Cl. ........................................ 382/304
(58) Field of Classification Search ............... 382/302, 382/304; 700/4, 5
See application file for complete search history.

(56) References Cited

U.S. PATENT DOCUMENTS

| 4,532,650 | A |   | 7/1985  | Wihl et al. |
| 4,681,442 | A |   | 7/1987  | Wagner |
| 5,185,812 | A |   | 2/1993  | Yamashita et al. |
| 5,274,717 | A | * | 12/1993 | Miura et al. ............ 382/304 |
| 5,699,477 | A |   | 12/1997 | McCree |
| 6,020,957 | A |   | 2/2000  | Rosengaus et al. |
| 6,122,046 | A |   | 9/2000  | Almogy |

OTHER PUBLICATIONS

International Search Report dated Jan. 7, 2004.

* cited by examiner

*Primary Examiner*—Vikkram Bali
(74) *Attorney, Agent, or Firm*—McDermott, Will & Emery

(57) ABSTRACT

A method and apparatus for parallel processing of data without the need for cross-communication or synchronization between processing nodes is provided. The system is especially suitable for use in a wafer inspection system for the semiconductor industry. Embodiments include scanning a small area of the wafer, and distributing pixel data among a plurality of processing nodes, each of which accept and process an optimal amount of pixel data independently of the other processing nodes, thereby enabling increased throughput without increasing system complexity.

2 Claims, 5 Drawing Sheets

HARDWARE CONFIGURATION FOR PARALLEL DATA PROCESSING WITHOUT CROSS COMMUNICATION

This application is a divisional of U.S. Application Ser. No. 09/726,597, filed Dec. 1, 2000, now U.S. Pat. No. 6,898,304.

FIELD OF THE INVENTION

This invention relates, generally, to hardware/software architecture for fast data processing, particularly useful for semiconductor wafer inspection systems.

BACKGROUND OF THE INVENTION

It is well known that in-process inspection of semiconductor wafers is crucial to achieving a high fabrication yield. To this end, sophisticated inspection technologies are utilized at various stages of device fabrication.

One such inspection system for semiconductor wafers is described in U.S. Pat. No. 5,699,477 (to Alumot et al.—hereinafter the Alumot system) whose contents is hereby incorporated herein by reference. The Alumot system includes a light source for scanning the wafer, and four photomultipliers (PMT) situated to form a dark field microscope. Each of the detectors provides data corresponding to a dark field image of a scanned region on the wafer. The data/images obtained from the detectors are processed to determine whether a defect exists on the scanned region. Such processing is generally known in the art as die-to-die, cell-to-cell and die-to-data base comparisons.

As is well known in the art, wafers are processed to create thereupon repetitive patterns such as dies, cells or portions thereof. As described in Alumot, the process of inspecting wafers includes successively scanning sections of the surface of the wafer and acquiring images representative of the scanned sections. The images are than subject to examination of repetitive patterns, comparing the examination results, and, on the basis of the results, identifying locations in the patterns that are suspected as defective.

Generally speaking, in a typical die-to-die inspection system, an image representative of a section of a wafer (e.g. a tile) is acquired and thereafter a pattern in the tile that falls in a given die is compared to a like pattern in succeeding die. Due to the repetitive nature of the patterns, both sections are expected to bring about substantially equal inspection results. If, however, an intolerable difference is encountered in the comparison of their images, this may suggest that a defect has been encountered. The examined patterns are not confined to a given size and may vary depending upon the inspection algorithm. Accordingly, the specified patterns may constitute any repetitive (or substantially repetitive) unit such as a die or portion thereof, cell or portion thereof, array of cells or portion thereof and/or others, all as required depending upon the particular application.

In the Alumot system the laser beam impinges the wafer at a 90 degree angle, and four detectors are used to provide four different perspectives of the image's location. Of course, other arrangements can be used to achieve similar results, and other detectors can be used to provide other images, such as a bright field image. An exemplary system is depicted in FIG. 5 herein. Specifically, a light beam source 500 is provided at a grazing angle to a wafer 510. Four PMTs 520, 525, 530 and 535, are also provided at a grazing angle, but are arranged spatially away from the normal reflection direction (i.e., Snell's Law reflection) of light beam 545. Thus, four detectors 520, 525, 530, 535 provide dark field images from four perspectives in the form of continuous data streams. An additional dark field detector 550 is situated at 90 degrees to the wafer's surface. A bright field detector 540 receives the normal reflection beam 545. Bright field detector 540 may be a point sensor or a plurality of light sensors, such as a CCD.

The above-described inspection systems typically require advanced and fairly complicated hardware and software implementation due to the small structures to be inspected. Moreover, since wafer inspection is performed during fabrication, another important requirement of these inspection systems is high throughput. Such high level computational requirements and high throughput requirements necessitate development of very sophisticated data processing schemes. For example, to increase the throughput of the above-described systems, fast data processing capability is needed to process the data received from all the detectors. One conventional way of increasing processing speed is to introduce parallelism into the computation. However, a sufficiently high level of parallelism disadvantageously introduces complexity to the hardware/software architecture of the system, since it requires addressing issues such as synchronization between concurrent tasks, exchange of data between tasks, etc. For example, while it is desirable to introduce parallelism by processing the data from each detector separately, such an approach requires difficult and complex synchronization between the various processing tasks to ensure matching of the pixel streams.

There exists a need for a data processing methodology that avoids increasing the complexity that is normally involved in realizing parallel sub-tasks. Specifically, a methodology is needed that enables parallel processing without synchronization.

SUMMARY OF THE INVENTION

An advantage of the present invention is a method and apparatus for inspecting patterned articles such as semiconductor wafers wherein collected data is processed in parallel as several data streams without synchronizing the data streams.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by a method for inspecting a surface of an article, the method comprising scanning a predetermined section of said surface to collect data; arranging the data as a two-dimensional array of data elements; dividing the data into columns; dividing each data column into a plurality of data blocks; providing a plurality of processing nodes, each processing node corresponding to one of the data blocks; and processing the data blocks substantially simultaneously using the corresponding processing nodes, wherein each processing node performs the processing independently of the other processing nodes.

Another aspect of the present invention is an apparatus for parallel processing of a data stream, comprising a data formatter for receiving a data stream and constructing therefrom a plurality of data lines, said data formatter comprising n output lines, each outputting respective 1/n of each of the data lines; and n processing groups, each comprising m processing nodes commonly connected to one of the n lines, wherein each of the m processing nodes is for processing approximately 1/m of the data flowing in one of the n lines substantially simultaneously and independently of the other processing nodes.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DETAILED DESCRIPTION OF THE INVENTION

Conventional techniques for parallel processing of data gathered during semiconductor wafer inspection require cumbersome synchronization schemes. The present invention addresses and solves this problem of conventional data processing techniques.

According to the methodology of the present invention, a scanned area of an article, such as a wafer section, is divided to sub-sections. A first processing node examines data representative of repetitive patterns in succeeding sub-sections, compares the results of the examined patterns and determines whether defect location(s) have been encountered. A similar operation is performed on data representative of other patterns substantially simultaneously by other processing nodes. However, the present methodology does not require cross communication between the processing nodes for data acquisition, because each node determines the data it is to process independently of the other nodes, thereby avoiding the need to synchronize operations between the nodes and to communicate between them. Accordingly, each node can independently reach a conclusion as to the existence of a suspected defect location and optionally classify the so detected location into a distinct defect category.

According to one aspect of the present invention, a scanned region is divided in the x and y directions for parallel processing. Specifically, separate data streams from various detectors of an inspection system, each representing an image in the form of pixels, are fed into a data formatting section ("DFS") which combines the data from the various detectors to generate vectors corresponding to each image pixel. The DFS then divides the combined data in the x direction to a specified number of parallel data streams, and outputs the data streams to a corresponding number of processing groups. Each of the processing groups comprises several processing nodes, which are used to divide the received data stream in the y direction. Using this structure, there is no need for cross communication between the processing nodes, or for synchronization between the processing nodes. Moreover, the software running in each node is the same, so only a single program needs to be written.

Figure 1:
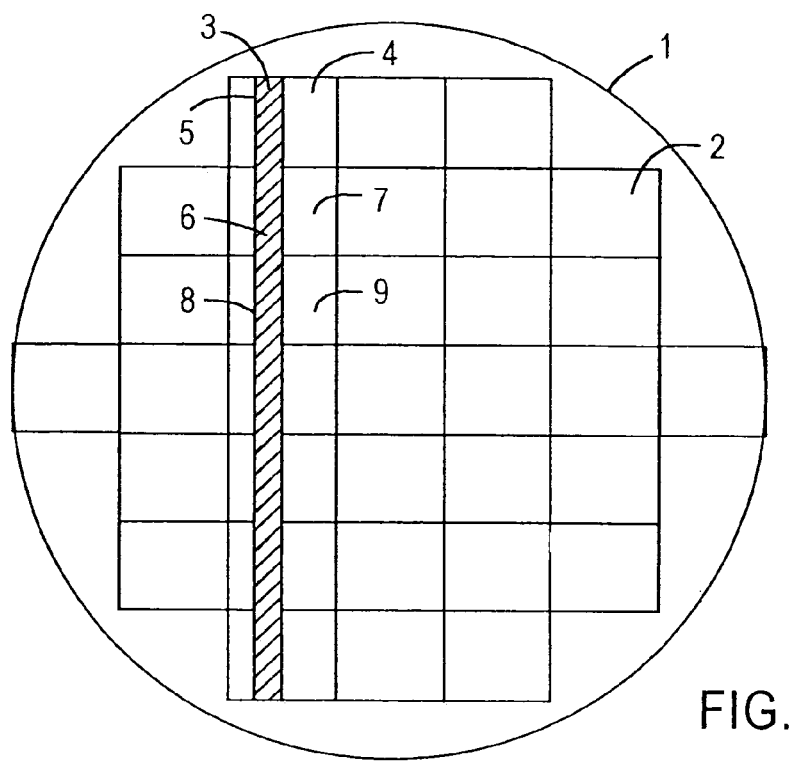
FIG. 1 is a schematic illustration of a wafer broken down by dies.

An embodiment of the present invention will now be described with reference to FIGS. 1–4. FIG. 1. illustrates a schematic illustration of a wafer 1 comprising a plurality of dies 2. Wafer 1 is scanned successively in a conventional manner, as with a laser light source 500 as described above, such that each of one or more detectors (e.g., detectors 520–535 and 550) produce a continuous stream of serial data, which is logically divided into lines, typically equal-length lines, although the lines do not need to be of equal length. In each cycle of scanning, data representative of a slice 3 of the surface of the wafer 1 is obtained. The data of slice sub-section 5 that is accommodated within a given die (e.g. die 4) comprises a known number of lines of data, and can be logically divided for processing into a plurality of repeating data sets 20, 21, 22 illustrated in FIG. 2. Other data sets (not shown) similar to sets 20, 21, 22, correspond to slice sections 6 and 8 in dies 7 and 9. As will be appreciated, for a small pixel size (i.e., high resolution) each data set may comprise a large amount of data which needs to be processed quickly. For example, data set 20 may comprise 2000 pixels in the x direction and 3000 pixels in the y direction, wherein each pixel can be represented by a vector which includes the data obtained from all the detectors for that particular point on the wafer 1.

Figure 2:
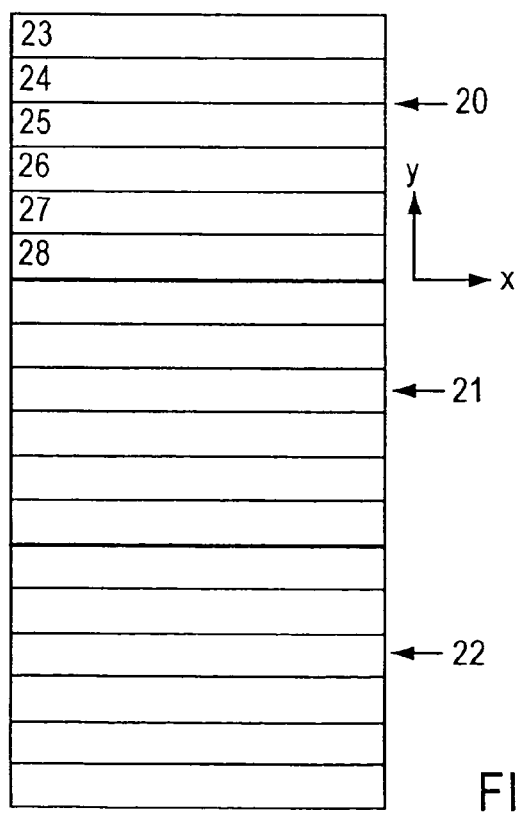
FIGS. 2 and 3 illustrate schematically a division of a section into sub-sections for performing parallel processing according to an embodiment of the invention.
Figure 3:
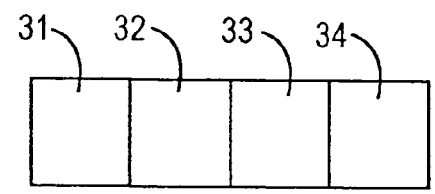

In this embodiment of the present invention, parallelism is introduced by logically dividing the continuous data stream from the detectors into several data streams along the $\chi$ direction. Each of these data streams is then divided into data sets such as data sets 20–22. Division in the x direction reduces the data rate of the continuous data stream from the detectors to processing nodes, which may otherwise be too high for any processing node to accept or even sample. This reduction of input data rate to each of the processing nodes also enables the use of common off-the-shelf acquisition/processing circuit boards, thereby reducing the cost of system hardware. Division in the y direction reduces the complexity of system interconnections, since a single line is spread over several nodes. As shown in FIG. 2, data set 20 is logically divided in the y direction into several data blocks 23–28.

Moreover, the DFS typically comprises a plural number of circuit boards or "cards" which cannot be connected in parallel in a single channel using only a division in the y direction, since the data rate for such a connection scheme would be too high. On the other hand, if the data sets are divided in only the x direction, an excessive number of physical connections are required between the DFS's cards and image processing cards, thereby increasing system interconnect complexity. Thus, the present invention reduces complexity, while maintaining high parallelism, by dividing the data in both x and y directions. An additional potentially significant benefit of the present invention's data division scheme is the reduction of undesirable redundant processing; that is, overlap between scans.

Referring again to FIGS. 2 and 3, each data set 20–22 is divided in the y direction into several data blocks 23 to 28 in set 20. Furthermore, each of the data blocks is divided in the x direction into several sub-blocks 31 to 34. In this example, each set is 2000×3000 pixels and is divided in the x direction by four and in the y direction by six, resulting in sub-blocks of 500×500 pixels. This approach creates a division into a large number of parallel processed data parts, in this example 24, while maintaining redundant processing to a minimum (in this example, 40 pixels).

Figure 4:
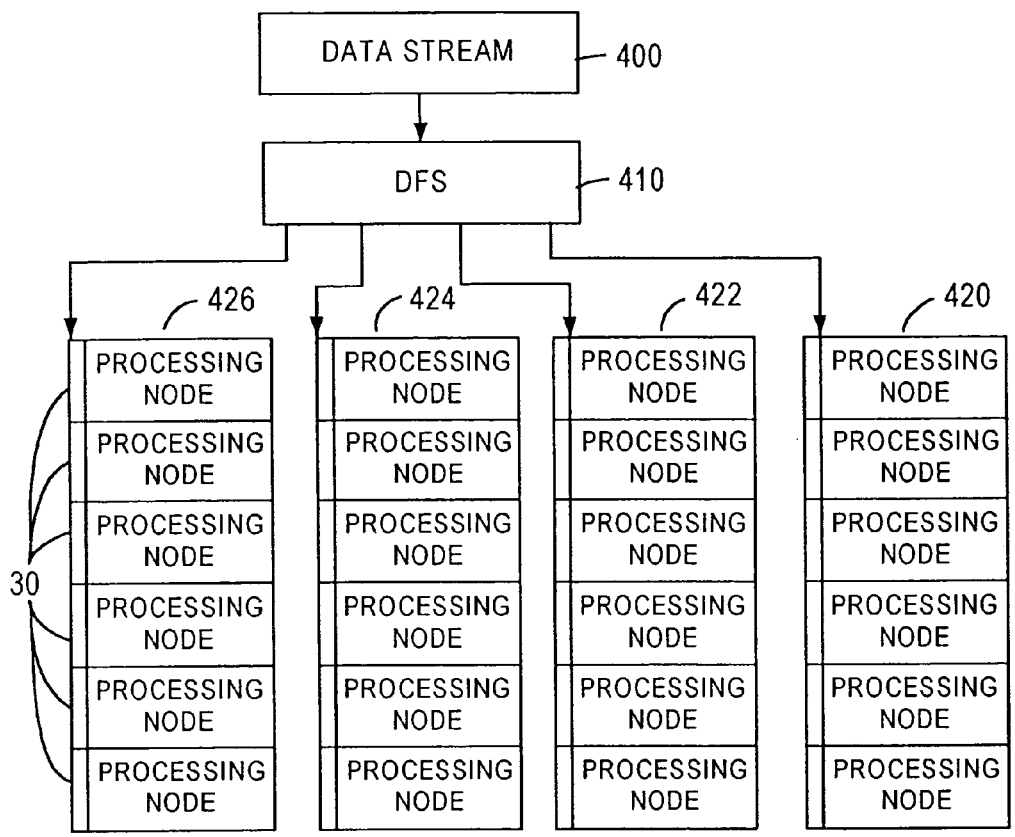
FIG. 4 is a block diagram of a system for realizing the parallel processing of FIGS. 2 and 3 according to an embodiment of the present invention.

FIG. 4 illustrates a hardware configuration for implementation of the above-described embodiment of the present invention; that is, for parallel processing of the data sub-blocks resulting from the division according to the above description. Each sub-block 31–34 constitutes a sub-section that is fed into a distinct processing node 430 for performing the examining and comparison operation. In the example shown in FIG. 4, 24 distinct processing nodes 430 are utilized, processing, substantially simultaneously, respective sub-blocks of a data set. Of course, depending on the desired processing power, each processing node 430 may comprise several microprocessors, such as Pentium II™ marketed by Intel Corporation. Typically, the 24 sub-blocks of set 20 are allocated to 24 respective processing nodes 430, each performing a processing task substantially independently. Thus, each processor of each node 430 has the same program, and no synchronization or cross-communication between the processors is needed. DFS 410 can comprise a plural number of data formatting boards, assembled from commonly available electronic components.

Figure 5:
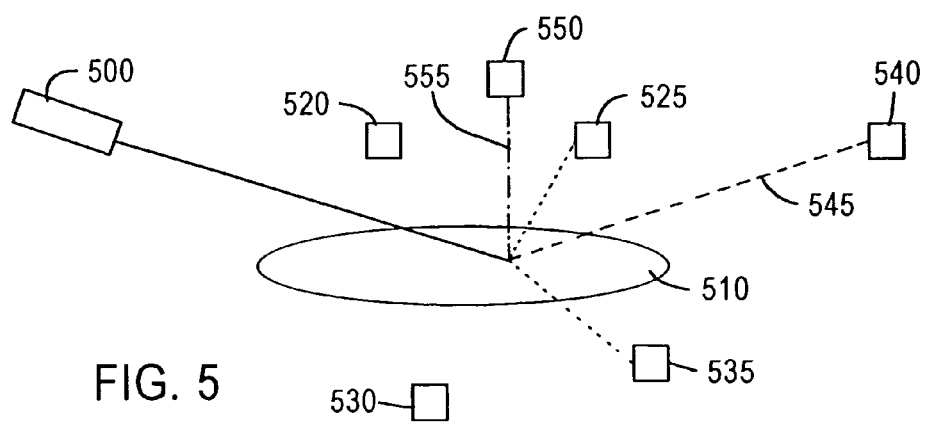
FIG. 5 schematically illustrates a wafer inspection system according to an embodiment the present invention.

Referring now to FIG. 5, a light source 500, such as a laser, together with appropriate optics, is used to scan a wafer 510. The scan is performed to cover successive slices (see slice 3 in FIG. 1). As is well known in the art, the scan in the x direction is done by appropriate optical elements, such as acousto-optic or mirror scanners, while the scan in the y direction is done by moving a stage (not shown). At each point during the scanning, image data is collected by all the available detectors 520–550.

Referring again to FIG. 4, the data collected from detectors 520–550 is depicted as data stream 400. At data formatting section ("DFS") 410, data stream 400 is grouped into pixels; i.e., every four data samples are grouped into a vector representing four perspectives of one pixel, or location, on the wafer. The result is a line of pixel data (i.e., line of vectors). In this specific example, each pixel data line is 2000 pixels wide. DFS 410 divides each line into four output lines, thereby creating the division in the x direction. Each of the output lines is fed to all of the processing nodes 430 in the respective processing groups 420–426. It will be clear to one skilled in the art that there are many different ways to perform the above-described steps of unifying several incoming data streams into vectors corresponding to physical locations, then cutting multi-byte lines of such "aspect vectors" along the x-direction. For example, the unification into vectors can be done in various different orders, the data can be fed in different formats, the lines can be cut differently, etc. Furthermore, input and output formats of DFS 410 can be different than in the embodiment of the present invention described herein. Therefore, it should be understood that the present invention is not limited to the embodiments described herein.

DFS 410 typically comprises several cards, configured depending on how it is desired to process data stream 400. For example, two cards can be configured such that the inputs of the cards are connected in parallel with four detectors, and each card outputs a predetermined number of lines; that is, instead of four output lines from a single card, two output lines come from one card and two from the other.

As shown in FIG. 4, each of the processing groups 420–426 includes six processing nodes 430. Each processing node 430 sees all of the line data fed to the processing group 420–426 to which it belongs, but processes only one sixth of the data. That is, assuming the lines for each data block, such as data block 23, are numbered 1–3000, then the first processing node 430 will accept for processing vectors belonging to lines 1–500, and reject 501–3000. During the time it sees and counts lines 501–3000 it can complete the appropriate processing for lines 1–500. When the count reaches 3001, it starts accepting data for processing again, until the count reaches 3500. A similar operation is performed by all processing nodes 430 in all of the processing groups 420–426. Thus, a division in the y direction is created.

The allocation of lines between parallel processing nodes 430 of FIG. 4, known as "load balancing", is important to the efficiency of the present invention, and is preferably carried out electronically by each processing node 430 using the load balancing methodology which will now be described.

As discussed above, wafer 1 is divided for scanning into slices 3 comprising an integer number of identical representations of dies called sub-sections 5, 6, 8 (also called "stripes"), which are further logically divided for processing into data blocks; e.g., data blocks 23–28. Each slice 3 has a finite and generally unpredictable number of lines, which must be divided into data blocks 23–28. Processing nodes 430 are grouped into processing groups 420–426 each having "m" number of nodes 430. Nodes 430 of the same processing group divide the scanned image in the y direction. Data stream 400 is composed of lines, assumed for purposes of this example to be of equal length, which are to be processed in parallel, each of the m processing nodes 430 of each processing group 420–426 handling 1 mn of all lines of the sub-section 5 being scanned.

According to the methodology of the present invention, each processing node 430 is capable of calculating the placement and size (in lines) of each data block 23–28 it is to process, without communicating with other nodes 430. The blocks should be sufficiently large to avoid unnecessary overhead (i.e., inefficiency) in the system, but not be so large as to create an uneven load distribution among the different processing nodes 430 and a consequent under-utilization of the system. The technique described below creates optimal load balance among processing nodes 430 by providing data blocks sized within a given range of lines, and differing from each other by at most one line in size in the y dimension (i.e., the least possible size difference).

The methodology assumes that the system knows the following parameters before the start of scanning of wafer 1:

| | |
|---|---|
| y_size: | y dimension size of a single sub-ssection 5 (also called die height); |
| min_size: | minimum allowable data block size, in lines, known from the parameters of the electronic hardware; |
| max-size: | maximum desired block size, in lines; and |
| num_nodes: | number of processing nodes 430 in a processing group 420–426. |

Additionally, prior to scanning wafer 1, processing nodes 430, which are intended to work in parallel and divide data stream 400 between them, are each given a unique identification number, ranging from 0 to (num_nodes−1).

The method's output is the number of lines in a data block 23–28, typically in the hundreds of lines. Since it is unlikely to always have an equal number of lines in each block 23–28, some of the blocks 23–28 will be one line larger than others to account for an unevenly divisible number of lines. The number of these "extended blocks" is also determined by the inventive method.

In the paragraphs that follow, "div" is the operation of division with a remainder, the result of which is a natural number. "mod" is a natural number which is the remainder of the "div" operation. For example, 13 div 5=2; 13 mod 5=3.

Figure 9:
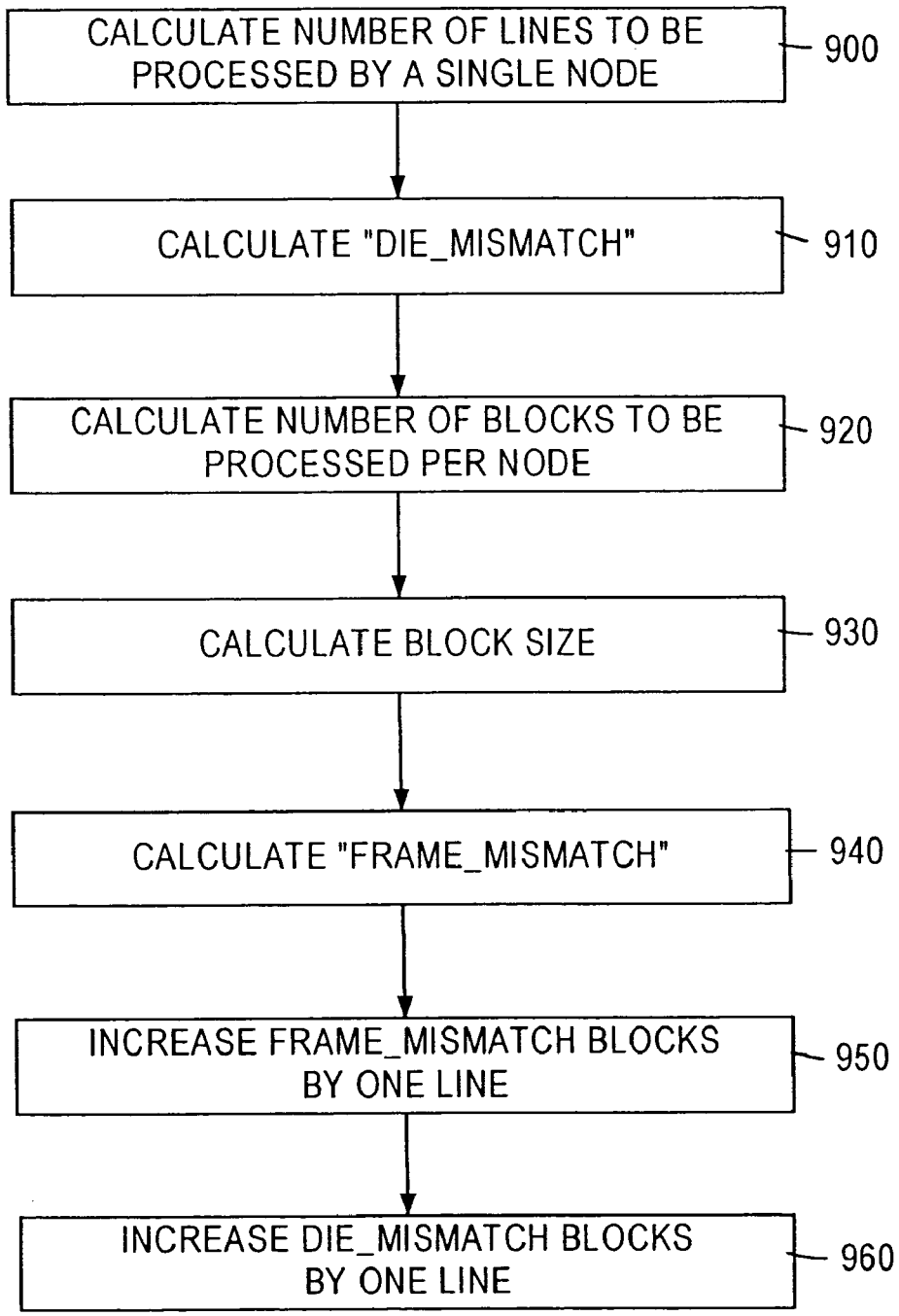
FIG. 9 is a flow chart illustrating a load balancing method according to the present invention.

Referring to the flow chart of FIG. 9, at step 900 the number of lines to be processed by a single processing node 430 ("num_lines_per_node") is calculated, and at step 910, a quantity called "die_mismatch", indicative of an excess (i.e., left over) number of lines at the level of partition of the subsection 5 between processing nodes 430, is calculated:

$$\text{num\_lines\_per\_node}=\text{y\_size div num\_nodes} \quad (1)$$

$$\text{die\_mismatch}=\text{y\_size mod num\_nodes} \quad (2)$$

At step 920, the number of data blocks 23–28 to be processed by a processing node 430 ("num_blocks_per_node") is calculated:

$$\text{num\_blocks\_per\_node}=\text{num\_lines\_per\_node div (max\_size}-1) \quad (3)$$

If num_lines_per_node mod (max_size−1) is not zero, increase num_blocks_per_node by one.

Note that "max_size−1" is used in equation (3) rather than simply "max_size" because, as discussed above, the size of some of the blocks 23–28 will need to be increased by one line to account for an uneven number of lines.

Next, the size of a data block 23–28 ("size_of_block") is calculated, in lines (see step 930), along with a quantity called "frame_mismatch", indicative of an excess number of lines at the level of partition of the processing node's lines into blocks 23–28 (see step 940):

$$\text{size\_of\_block}=\text{num\_lines\_per\_node div num\_blocks\_per\_node} \quad (4)$$

$$\text{frame\_mismatch}=\text{num\_lines\_per\_node mod num\_blocks\_per\_node} \quad (5)$$

It is assumed that the size of sub-section 5 exceeds the minimum block size min_size. In practice, this may not be the case. If so, the methodology can be adapted by processing several sub-sections 5, 6, 8 as a single "virtual sub-section".

As explained above, it is unlikely that the total number of lines (i.e., y_size) can be evenly distributed to each processing node 430, so size_of_block calculated in equation (4) is used as a minimum number of lines in each block 23–28. A certain number of lines is left over in each sub-section 5; namely, frame_mismatch lines are left over. To compensate for these remaining lines, exactly frame_mismatch blocks are increased in size by one line at step 950. This can be accomplished since frame_mismatch is always less than num_blocks_per_node.

Likewise, die_mismatch lines are also left over in each sub-section 5. Die_mismatch is always less than num_nodes, and one unincreased block 23–28 always exists in each processing node 430. Therefore, exactly die_mismatch nodes 430 increase one of their unincreased blocks 23–28 by one line to compensate for die_mismatch at step 960. For example, all processing nodes 430 having an identification number less than die_mismatch will increase one block 23–28 by one line at step 960.

Alternatively, for simplicity's sake, a variable called "threshold" can be defined for each node 430, which is equal to frame_mismatch if the identification number of the node is greater than or equal to die_mismatch, and equal to (frame_mismatch+1) otherwise. Each node 430 can thus calculate num_blocks, size_of_block and threshold independently of other nodes 430, then input from DFS 410 blocks 23–28 of the calculated size (i.e., size_of_block) wherein the first threshold number of blocks 23–28 are increased in size by one line.

Thus, each processing node 430 calculates the optimal number of lines it is to process independently of all the other nodes 430, based on its knowledge of the number of nodes in its group, the die height in lines, its own identification number, and the range of possible block sizes. Each processing node 430 then accepts exactly the calculated number of lines from DFS 410.

It should be recognized that data from DFS 410 can be divided by processing nodes 430 of a particular processing group 420–426 using other geometric arrangements than the one disclosed in this embodiment of the present invention. For example, a data stream to processing nodes 430 can be divided in both the x and y directions in addition to the DFS's division of the stream in the x direction. In such cases, the load balancing technique described above should still be employed to ensure optimal load distribution.

The particular processing of each pixel to detect defects is known and well documented in the Alumot patent, which states at column 10, lines 47 to 54:

"Detection of defects by the defect detector in each channel is based on the comparison of each pixel in the inspected stream with the corresponding reference stream.-" As indicated by this passage, the comparison between pixels for the purpose of defect detection is performed on a pixel-to-pixel basis which complies with the "local" nature that facilitates mutually independent parallel processing of the invention.

In the above noted example, each processing node 430 makes a determination with respect to each pixel, i.e., whether it is defective or not, independently of the other processing nodes. The output of all processing nodes 430 is then combined to provide a defect map, i.e., a mapping of suspected defect locations on the inspected wafer.

Figure 6:
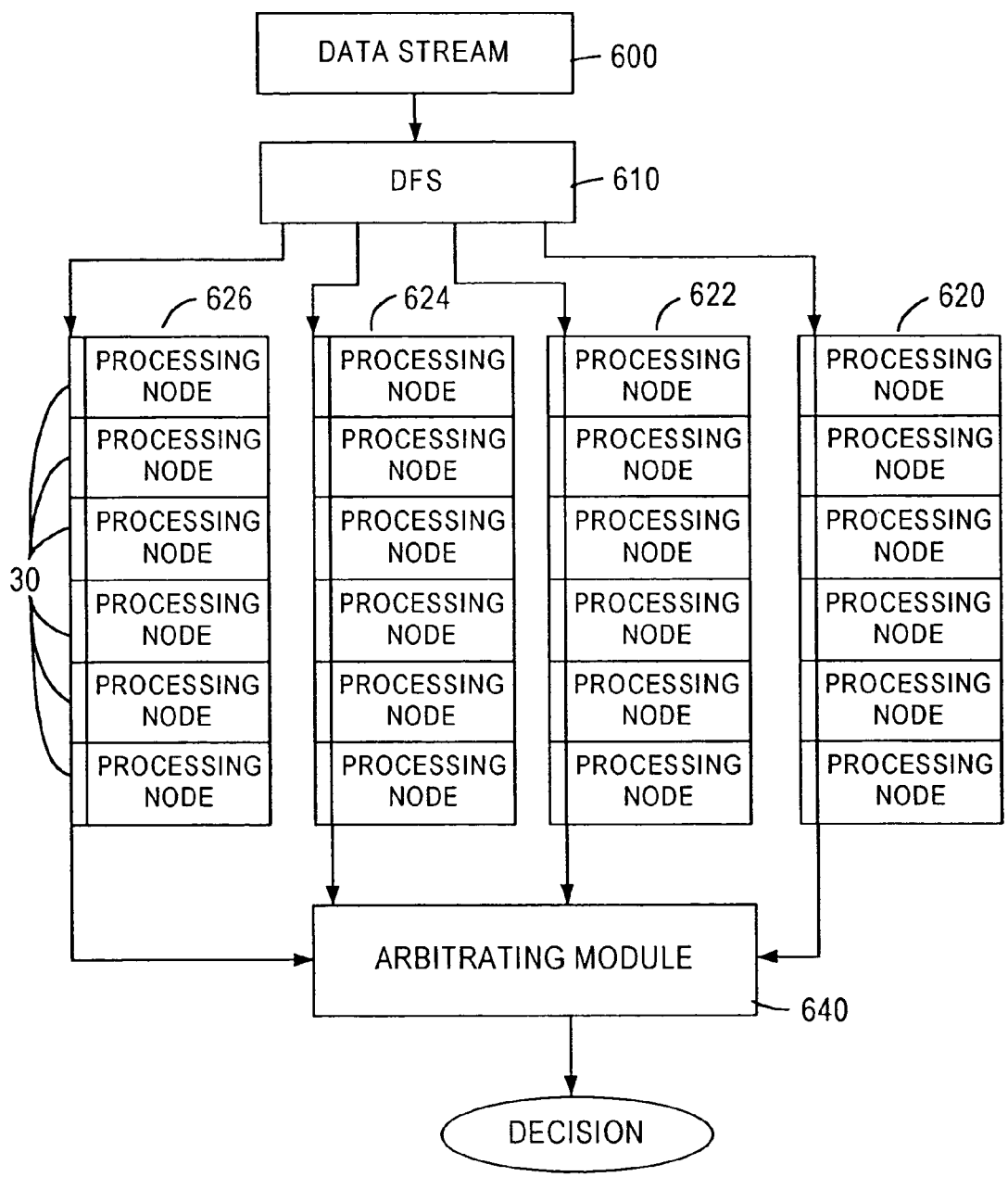
FIG. 6 is a block diagram of a system for realizing the parallel processing of FIGS. 2 and 3 according to another embodiment of the present invention.

According to another embodiment of the present invention, the number of processing groups equals the number of sensors. This embodiment is exemplified in FIG. 6, wherein it is assumed that the system has four sensors. According to such an embodiment, DFS 610 divides incoming data stream 600 according to sensors, rather than pixels. More specifically, DFS 610 outputs every fourth data point to a specified processing group 620–626.

Thus, for example, incoming data points 1, 5, 9, etc. will be sent to processing group 626; points 2, 6, 10 etc. to processing group 624, and so on.

Consequently, in this system each processing node makes a decision with respect to a pixel and only one sensor data. That decision is output from all processing nodes 630 to arbitrating module 640. Depending on the algorithm used, arbitrating module 640 takes the decision of processing nodes 630 with respect to each given pixel, and makes a final determination as to whether it is a suspect pixel. For example, arbitrating module 640 can be programmed so that, with respect to a given pixel, if two or more processing nodes 630 provided a "suspect" determination, it is declared as a defect. Of course, a more elaborate algorithm can be used, for example, arbitrating module 640 can also consider neighboring pixels and, if a neighboring pixel was declared as defect, a suspect indication from only a single processing node 630 can lead to a defect determination.

Figure 7:
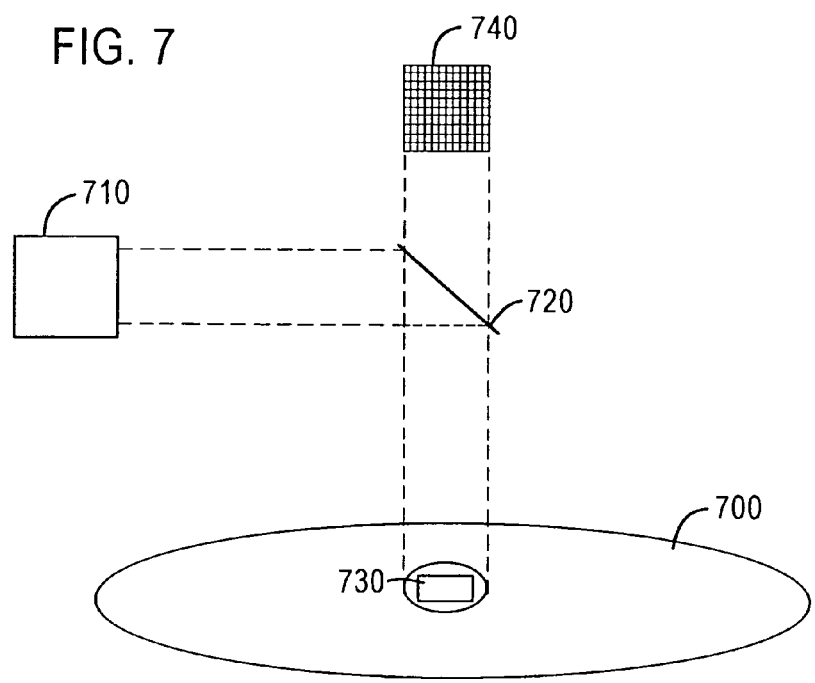
FIG. 7 schematically illustrates a wafer inspection system according to yet another embodiment the present invention.

A further embodiment of the present invention is depicted in FIG. 7. Specifically, wafer 700 is illuminated using a light source 710 which provides a rather large illumination spot, 730, on wafer 700. In this example, the light is deflected onto wafer 700 using a dichroic mirror 720, but of course, other methods for illuminating the wafers can be used. An image of the illuminated area 730 is then constructed by scanning using a conventional TDI sensor 740, which images an object one line at a time. For example, TDI sensor 740 may be 2048 pixels wide and have 2048 output taps.

It is conventional to group the output taps of a TDI into groups of, say 16 taps in a group, and process each group separately. In certain applications, such as in wafer inspection, such grouping still places high demands on the image processing system. Therefore, using the present invention, the processing of the data from the TDI is accomplished by sampling the data from the output taps in groups, and sending the data from each group to a respective processing group 420–426 of FIG. 4 (i.e., the number of processing groups equals the number of tap groups). As in the other embodiments of the present invention described above, each processing node 430 makes an independent decision with respect to each received pixel (in this case, with respect to each segment of the image for which the processing node is responsible). In this embodiment, the division in the x direction is according to the TDI tap groups (i.e., according to the output taps of TDI sensor 740), while the division in the y direction is done by dividing the image into segments (i.e., each processing node processes a predetermined number of scanned lines).

Figure 8:
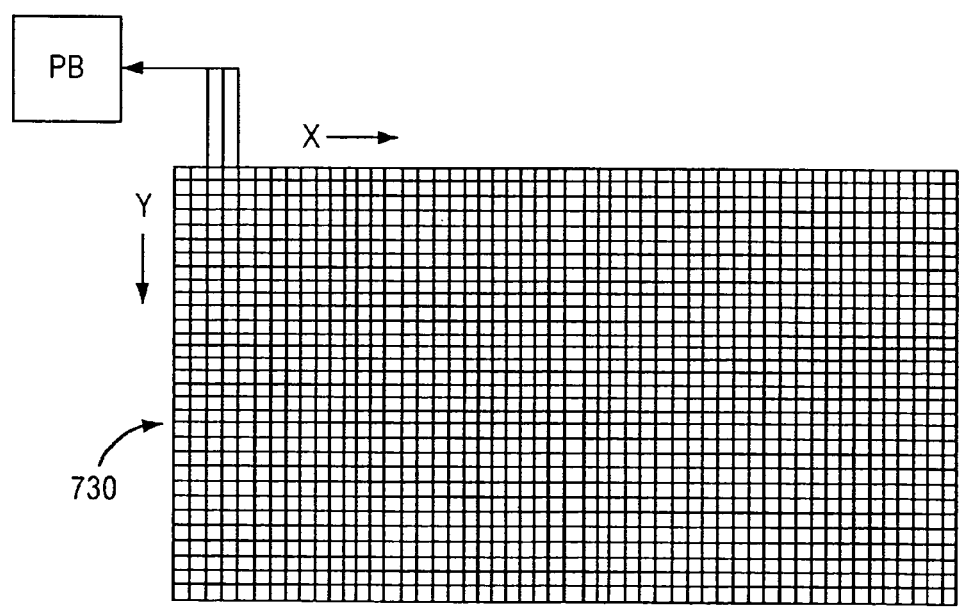
FIG. 8 is an enlarged view of the scanned area of FIG. 7.

Scanned area 730 of FIG. 7 is enlarged in FIG. 8. The X-direction is chosen along the width of TDI sensor 740; i.e., along the taps, while the Y-direction is chosen along the scan lines. While each of the taps has an output line, for clarity, only three output lines are depicted in FIG. 8. The three outputs depicted in FIG. 8 represent one grouping of output taps. Preferably, such a grouping would consist of 16 or 32 output taps. The grouping is sent to a corresponding processing group PB comprising several processing nodes 430 as shown, for example, in FIG. 4. Each of processing nodes 430 processes the data from all the output taps in the assigned group, but only for a specific number of scanned lines. That is, it counts the line numbers in the Y-direction, and processes only the number of lines under its responsibility. Consequently, each processing node 430 processes only a segment of the entire scanned image.

When the described TDI system is used for inspection of patterned wafers, it is preferable that each of the processing nodes collect and store data relating to an assigned image segment of a first die on the wafer, then collect data relating to an assigned image segment of a second die on the wafer. The data of the first image is subtracted from the data of the second image to obtain a difference image segment. The gray level of each pixel of the difference image is then checked to determine whether its gray level value exceeds a threshold. If so, that pixel is designated as representing a defect.

The present invention requires substantially no synchronization and exchange of communication between processing nodes and, consequently, each processor is capable of conducting its processing task substantially independently. Moreover, by dividing the data sets in both the x and y direction, optimal data rates and simple interconnect schemes are achieved.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An apparatus for parallel processing of a data stream, comprising:
    a data formatter for receiving a data stream and constructing therefrom a plurality of data lines, said data formatter comprising n output lines, each outputting respective 1/n of each of the data lines; and
    n processing groups, each comprising m processing nodes commonly connected to one of the n lines,
    wherein each of the m processing nodes is for processing approximately 1/m of the data flowing in one of the n lines substantially simultaneously and independently of the other processing nodes;
    wherein each processing node is for processing the approximately 1/m of the data as a plurality of data sub-blocks substantially simultaneously, each sub-block comprising a maximum number "max_size" of lines, and
    wherein each node has an identification number and a processor configured to perform the steps of:
    calculating a nominal number of lines to be processed by each node and an excess "mismatch_1" number of lines based on the plurality of data lines and the number of nodes m per processing group;
    calculating a number of sub-blocks to be processed per node based on max_size and the nominal number of lines per node;
    calculating a nominal size, in lines, of the sub-blocks and an excess "mismatch_2" number of lines based on the nominal number of lines per node and the number of sub-blocks per node;
    increasing the size of a mismatch_2 number of sub-blocks by one line; and
    increasing the size of the node by one line based on mismatch_1 and the node identification number.

2. An apparatus for parallel processing of a data stream, comprising:

a data formatter for receiving a data stream and constructing therefrom a plurality of data lines, said data formatter comprising n output lines, each outputting respective 1/n of each of the data lines; and n processing groups, each comprising m processing nodes commonly connected to one of the n lines, wherein each of the m processing nodes is for processing approximately 1/m of the data flowing in one of the n lines substantially simultaneously and independently of the other processing nodes;

wherein each processing node is for processing the approximately 1/m of the data as a plurality of data sub-blocks substantially simultaneously, each sub-block comprising a maximum number "max_size" of lines, and wherein each node has an identification number and a processor configured to perform the steps of:

calculating a nominal number of lines to be processed by each node and an excess "mismatch_1" number of lines based on the plurality of data lines and the number of nodes m per processing group;

calculating a number of sub-blocks to be processed per node based on max_size and the nominal number of lines per node;

calculating a nominal size, in lines, of the sub-blocks and an excess "mismatch_2" number of lines based on the nominal number of lines per node and the number of sub-blocks per node;

determining a variable "threshold", wherein threshold is equal to mismatch_2 when the node identification number is greater than or equal to mismatch_1, and threshold is equal to mismatch_2+1 when the node identification number is less than mismatch_1; and increasing the size of a threshold number of sub-blocks by one line.

* * * * *